(12) United States Patent
Khan

(10) Patent No.: US 10,786,347 B1
(45) Date of Patent: Sep. 29, 2020

(54) SCLERAL BELT AND METHOD

(71) Applicant: Mehdi Ali Khan, Clarence Center, NY (US)

(72) Inventor: Mehdi Ali Khan, Clarence Center, NY (US)

( * ) Notice: Subject to any disclaimer, the term of this patent is extended or adjusted under 35 U.S.C. 154(b) by 155 days.

(21) Appl. No.: 16/186,970

(22) Filed: Nov. 12, 2018

Related U.S. Application Data

(60) Provisional application No. 62/711,254, filed on Jul. 27, 2018, provisional application No. 62/658,663, filed on Apr. 17, 2018.

(51) Int. Cl.
*A61F 2/14* (2006.01)
*A61F 9/00* (2006.01)

(52) U.S. Cl.
CPC .................. *A61F 2/14* (2013.01); *A61F 9/00* (2013.01); *A61F 2220/0033* (2013.01)

(58) Field of Classification Search
CPC .... A61F 2/14; A61F 9/00; A61F 9/007; A61F 9/00727
See application file for complete search history.

(56) References Cited

U.S. PATENT DOCUMENTS

| | | | |
|---|---|---|---|
| 9,962,255 B1* | 5/2018 | Weiss | A61F 2/14 |
| 2003/0139808 A1* | 7/2003 | Shahinpoor | A61F 2/147 623/4.1 |
| 2006/0167422 A1* | 7/2006 | Shahinpoor | A61F 9/00727 604/294 |
| 2010/0305694 A1* | 12/2010 | Lee | A61F 9/00727 623/6.63 |
| 2014/0074128 A1* | 3/2014 | Park | A61K 9/0051 606/151 |

OTHER PUBLICATIONS

Ricci et al., "Octyl 2-cyanoacrylate tissue adhesive in experimental scleral buckling," Acta Ophthalmol. Scand. 2001: 78: 506-508 (Year: 2001).*

* cited by examiner

*Primary Examiner* — Thaddeus B Cox
(74) *Attorney, Agent, or Firm* — Phillips Lytle LLP; David L. Principe

(57) ABSTRACT

A scleral belt with an elongate strap having a first end and a second end. The strap has a plurality of openings disposed near the first end. A loop is disposed near the second end of the strap. A frame may be pivotally attached at the second end. The frame supports a prong which is pivotally attached to the frame. The first end of the strap passes through the frame and the loop, and the prong engages with one of the openings to fix the position of the two ends of the strap. The operation of the improved scleral belt makes it easier to adjust the scleral belt to adjust the height and location of the "buckling effect."

15 Claims, 4 Drawing Sheets

SCLERAL BELT AND METHOD

CROSS-REFERENCE TO RELATED APPLICATION

The present application claims priority benefit of U.S. Provisional Patent Application No. 62/658,663 entitled "Scleral Belt and Method" filed on Apr. 17, 2018, and U.S. Provisional Patent Application No. 62/711,254 entitled "Scleral Belt and Method" filed on Jul. 27, 2018, both of which are hereby incorporated by reference.

TECHNICAL FIELD

The present invention relates generally to the field of treatments for retinal detachment, and more particularly to a scleral belt and a method of using such a device.

BACKGROUND ART

The most common type of retinal detachment is rhegmatogenous retinal detachment (RRD) and is caused by liquefied vitreous passing through a retinal break into the potential space between the retinal and retinal pigment epithelial (RPE) layer leading to visual loss, which can be permanent, if left untreated.

A scleral buckle is a medical device permanently attached around the outside of the eye for repairing a detached retina. The scleral buckle is an elongate member with a body having a first end and a second end disposed opposite from the first end. The body is typically provided with a loop near the second end. The body is positioned around the outside of the eye, and the first end is threaded through the loop. The first end is then attached to the body near the second end by suturing the first end onto the body in overlapping fashion.

BRIEF SUMMARY OF THE INVENTION

With parenthetical reference to the corresponding parts, portions or surfaces of the disclosed embodiment, merely for the purposes of illustration and not by way of limitation, in one embodiment the present invention provides a scleral belt (10) with an elongate strap (13) having a first end (16) and a second end (19). The strap (13) has a plurality of openings (22) disposed near the first end (16). A loop (25) is disposed near the second end (19) of the strap (13). A frame (28) may be pivotally attached at the second end (19). The frame (28) supports a prong (31) which is pivotally attached to the frame (28). The first end (16) of the strap (13) passes through the frame (28) and the loop (25), and the prong (31) engages with one of the openings (22) to fix the position of the two ends (16), (19) of the strap (13). The operation of the improved scleral belt (10) makes it easier to adjust the scleral belt (10).

In another aspect of the invention, the scleral belt (10) is typically held in position around the outside of the eye by placing it underneath the muscles which form natural anchor positions. In the spaces between the muscles, additional loops (11) for holding the scleral belt (10) in position may be formed by attaching loops (11) to the outside of the eye by means of a biocompatible adhesive. Once the loops (11) are attached, the scleral belt (10) can be threaded through the loops (11) between the muscle positions. In another embodiment of the invention a positioning member (100) has a base (103) with a pair of loops (106) attached thereto for receiving the scleral belt (10). The base (103) may be curved at the bottom surface (104) and may be provided with a layer (109) of biological adhesive for holding the positioning member (100) against the eye of the patient. The positioning member (100) may also be provided with a strap (112) having a ratcheting mechanism (115) for tightening the strap (112) against the belt (10).

DESCRIPTION OF THE PREFERRED EMBODIMENTS

Figure 1:
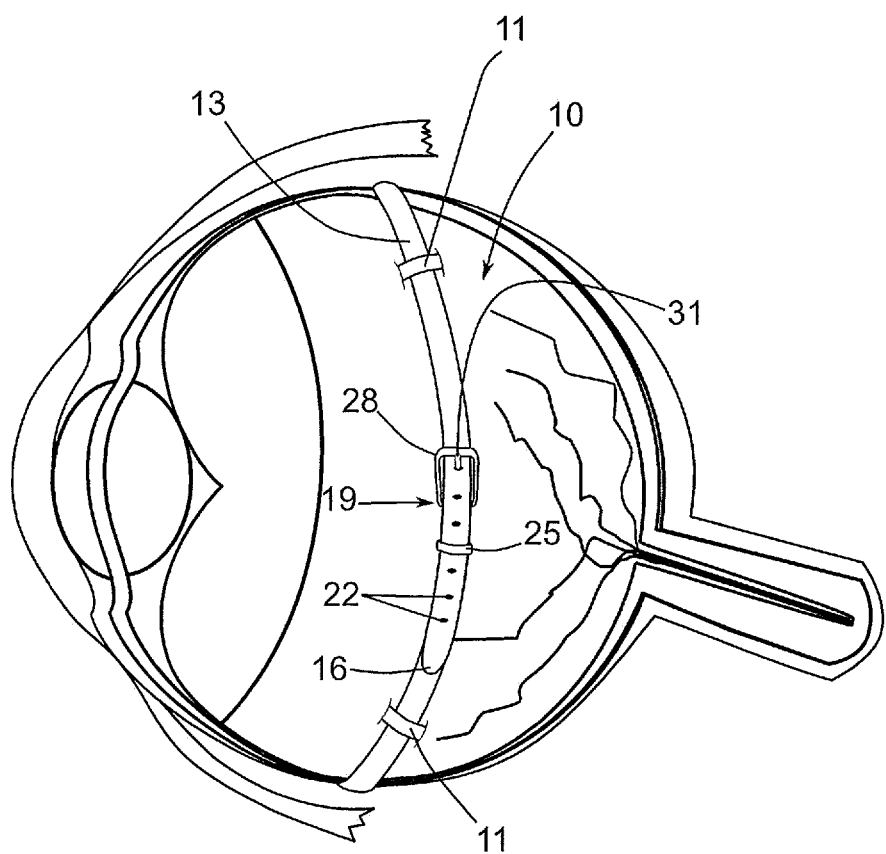
FIG. 1 is a perspective view of the eye of a patient with the scleral belt of the present invention disposed around the outer circumference of the eye.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Management of RRD type retinal detachments may be accomplished as follows. First, all retinal breaks are located. Second, a chorio-retinal irritation is created around each break. Third, the retinal and choroid are brought into contact for sufficient time to produce a chorio-retinal adhesion to permanently close the break.

The retinal breaks can be closed by a number of methods. A scleral buckle indents the sclera (from the outside and beneath the retinal breaks) and promotes re-apposition of the retina to the RPE by reducing vitreous traction and diminishing the flux of sub-retinal vitreous through the retinal tear. The indentation of the scleral buckle may change the vector of tractional forces and therefore reduces the traction on the breaks.

Choosing a scleral buckle technique is a decision based on many factors. The number and position of the retinal breaks, the size of the eye, the preference of the surgeon, and associated vitreo-retinal findings may all be considered. If intra-ocular pressure increases due to displaced volume from the buckling effect, external drainage of sub-retinal fluid, readjusting the height of the scleral buckle and/or intraocular gas tamponade may be indicated.

The general technique for treating a retinal detachment is as follows. A conjunctival opening may be performed near the limbus (360 degrees). Blunt dissection is performed using curved scissors. Localized bleeding is controlled using a hand held cautery. All four recti muscle are identified and isolated using silk suture. Retinal tears are carefully identified and cryopexy is performed around the tears using an indirect opththalmascope. No aspect of a scleral buckling procedure is more important than placement of the buckle (location and height of buckle) on the sclera. This procedure requires precise localization of retinal breaks on the scleral surface.

Instead of a scleral buckle, placement of a scleral belt accurately on the scleral, according to the present invention, will offer ease of readjusting and location and height of the "buckling effect."

Referring now to the drawings, and more particularly to FIG. 1 thereof, this invention provides a scleral belt 10 formed from an elongate strap 13 having a first end 16 and a second end 19. The first end 16 and the second end 19 may be disposed in overlapping fashion to provide a continuous loop surrounding the sclera. The circumference of the loop may be adjusted by adjustably connecting the first end 16 to the second end 19. The first end 16 may be connected to the second end in many ways including for example a frame 28 and prong 31 style as shown in the figure. In the alternative, the first end 16 and second end 19 may be connected by a free end and a pair of loops on the opposite end for securing the free end. Other configurations such as a plurality of teeth on one end and a pawl or tongue on the opposite end that engages with the teeth may also be suitable.

The purpose of the adjustable locking mechanism is to provide for manual adjustment of the position of the first end 16 relative to the second end 19 and may be accomplished in a variety of ways as will be evident to those of ordinary skill in the art based on this disclosure.

As shown in FIG. 1, in one example of the mechanism for adjustably connecting the ends 16 and 19, the strap 13 has a plurality of openings 22 near the first end 16. A loop 25 is disposed near the second end 19 of the strap 13. The frame 28 is pivotally attached at the second end 19. The frame 28 supports the prong 31 which is pivotally attached to the frame 28. The first end 16 of the strap 13 passes through the frame 28 and the loop 25, and the prong 31 engages with one of the openings 22 to fix the position of the two ends 16, 19 of the strap 13. The operation of the improved scleral belt 10 makes it easier to adjust the location and height of the "buckling effect."

In another aspect of the invention, the scleral belt 10 is typically held in position around the outside of the eye by placing it underneath the muscles which form natural anchor positions. In the spaces between the muscles, additional loops 11 for holding the scleral belt 10 in position may be formed by attaching loops 11 to the outside of the eye by means of a biocompatible adhesive. Once the loops 11 are attached, the scleral belt can be threaded through the loops 11 between the muscle positions.

Figure 2:
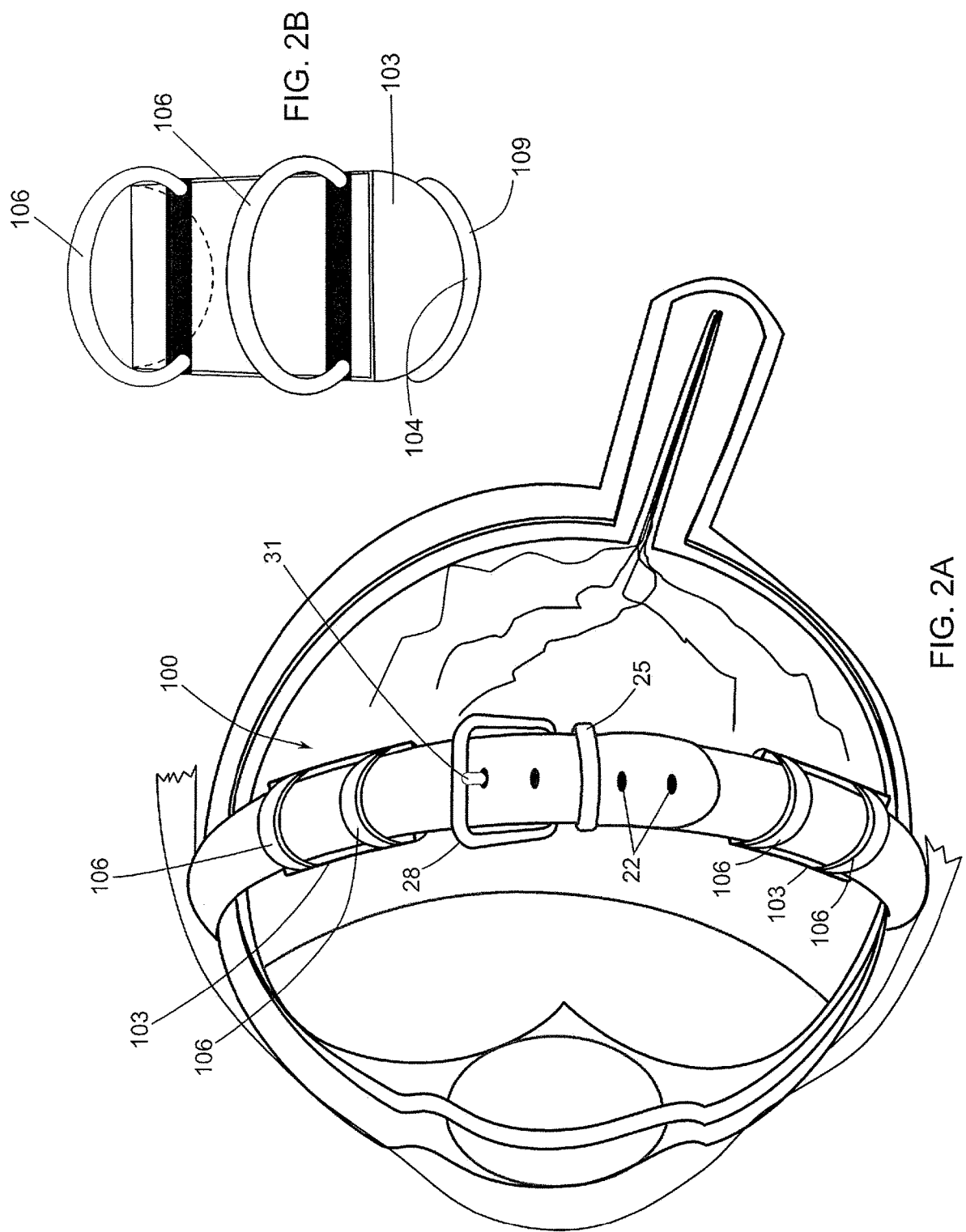
FIG. 2A is a perspective view of the eye of a patient showing a second embodiment of the invention.
FIG. 2B is a perspective view of the positioning member of the second embodiment.

Turning to FIGS. 2A-2B, as an alternative to the loops 11 shown in FIG. 1, a positioning member 100 has an elongate base 103 with one or more loops 106 attached thereto for receiving the scleral belt 10. The scleral belt 10 may be oriented parallel to a longitudinal axis of the base 103. The base 103 has an upper surface that receives the belt 10 and a bottom surface 104 that faces the eye of the patient. The one or more loops 106 may be constructed from an elastomeric material capable of stretching to receive the belt 10 and then maintaining a compressive force on the belt 10 to hold it in place in the positioning member 100. The base 103 may be curved at the bottom surface 104 and may be provided with a layer 109 of biological adhesive for holding the positioning member 100 against the eye of the patient. The positioning member 100 provides a structure for holding the belt 10 in place against the eye and eliminates the requirement for attaching the additional loops 11. The combination of the force of the strap 13 against the positioning member 100 and the biological adhesive aid in maintaining the position of the device on the sclera.

Figure 3:
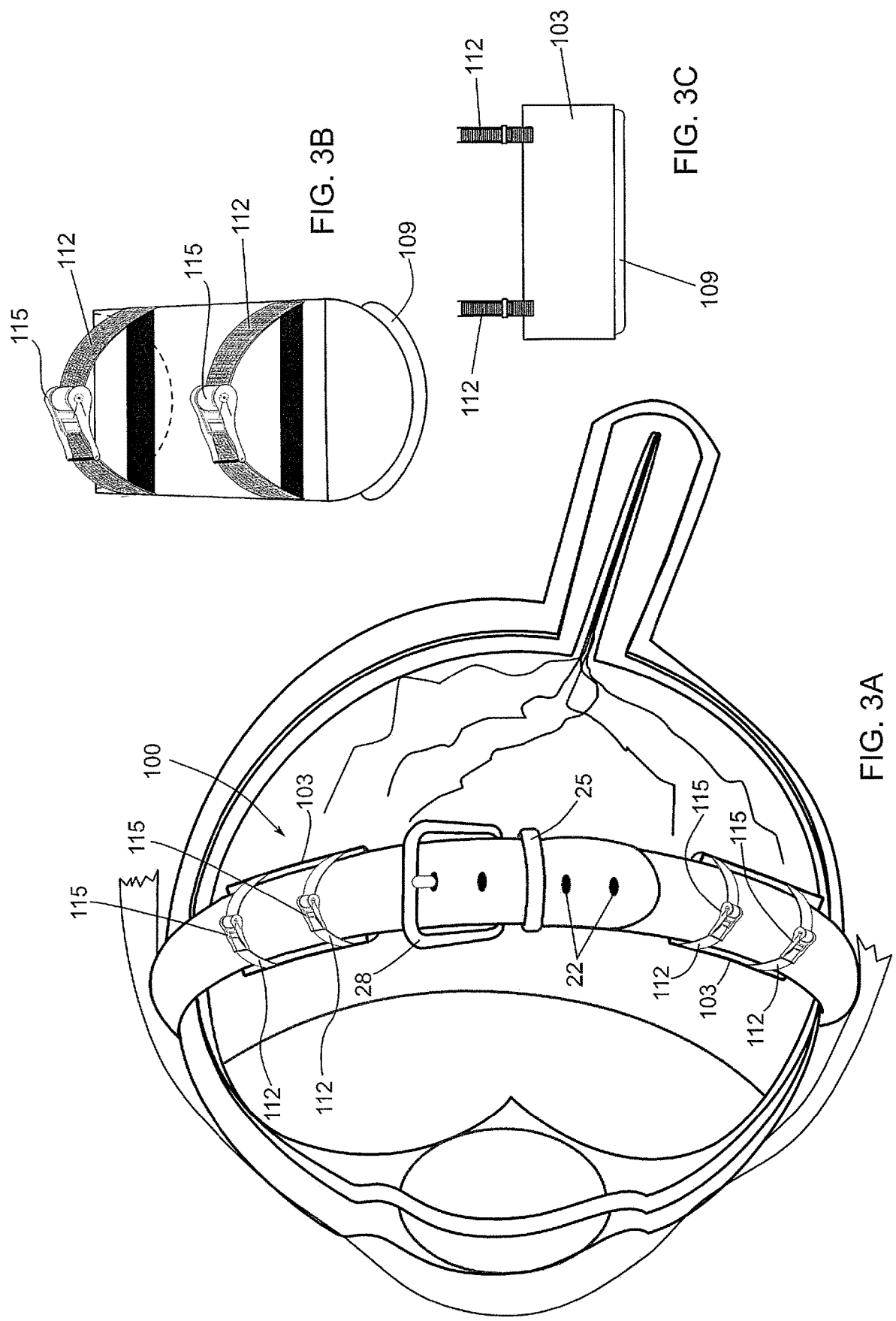
FIG. 3A is a perspective view of a third embodiment of the present invention.
FIG. 3B is a perspective view of an alternate embodiment of the positioning member of the present invention.
FIG. 3C is a side elevational view of the positioning member shown in FIG. 3B.

Turning to FIGS. 3A-3C, as an alternative to the elastomeric loops 106, the positioning member 100 may be provided with a pair of straps 112 having a ratcheting mechanism 115 for tightening the strap 112 downward against the belt 10 to hold the strap 13 of the belt 10 in a fixed position relative to the positioning member 100. The positioning member 100 shown in FIGS. 3A-3C may also be provided with a layer 109 of biological adhesive for attaching the positioning member 100 to the eye of the patient.

Figure 4:
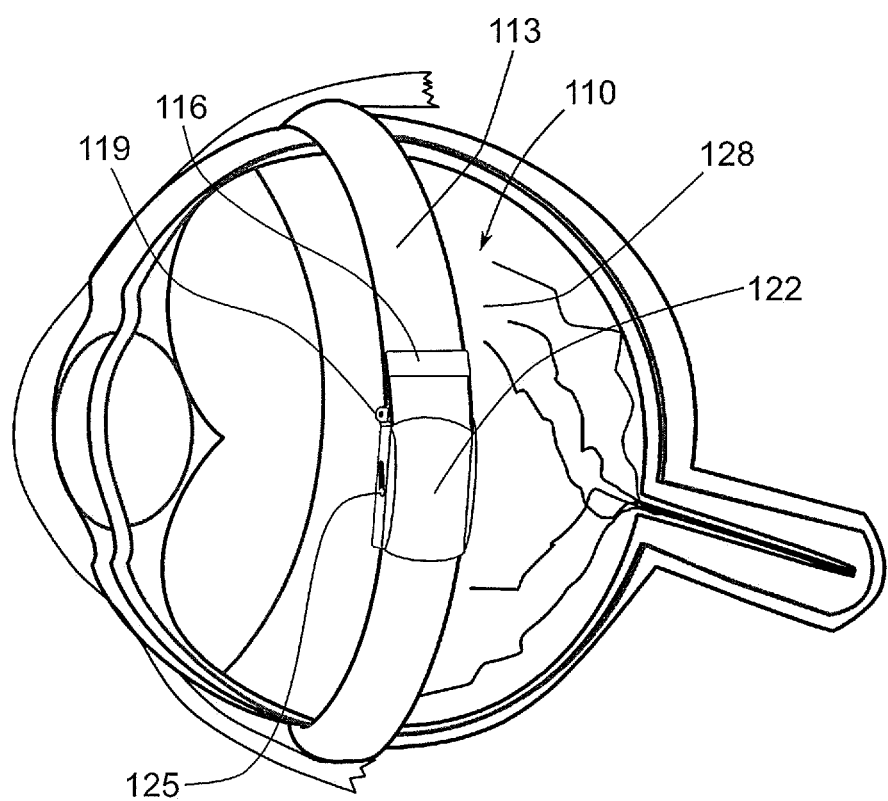
FIG. 4 is another embodiment of the scleral belt of the present invention.

Turning to FIG. 4, a scleral belt 110 with a strap 113 includes a first end 116 and a second end 119 disposed opposite from the first end 116. A buckle 122 may be attached at the second end 119. The buckle 122 may be provided with a sliding pin 125 that allows the belt 110 to be cinched into place on the sclera 128. The sliding pin 125 provides for securing the two ends 116, 119 together and may be adjusted to increase or decrease the circumference of the belt 110 during use. The belt 110 may be provided with a positioning device to assist in maintaining the position of the belt 110 on the sclera 128. The positioning device may comprise any of the positioning devices shown in FIGS. 1-3C, i.e., the loop 11 of FIG. 1, positioning member 100 of FIGS. 2A-2B and 3A-3C.

The present invention contemplates that many changes and modifications may be made. Therefore, while the presently-preferred form of the scleral belt has been shown and described, and several modifications and alternatives discussed, persons skilled in this art will readily appreciate that various additional changes and modifications may be made without departing from the spirit of the invention.

What is claimed is:

1. An apparatus for providing a compressive force to a sclera of a patient, the apparatusy comprising:
   a strap sized to fit around the outer surface of the sclera, the strap having a first end and a second end disposed opposite the first end;
   a plurality of openings disposed on the strap near the first end;
   a frame attached to the second end of the strap;
   a prong pivotally attached to the frame;
   a loop disposed on the strap near the second end of the strap;
   wherein the first end passes through the frame and the loop and the prong engages with one of the openings to fix the position of the first end relative to the second end.

2. The apparatus of claim 1, wherein the frame is pivotally attached to the second end of the strap.

3. The apparatus of claim 1, further comprising a second loop configured to be attached directly to the sclera by a biocompatible adhesive.

4. The apparatus of claim 3, wherein a portion of the strap is disposed through the second loop.

5. The apparatus of claim 1, further comprising a positioning device having a first surface and a second surface disposed opposite the first surface.

6. The apparatus of claim 5, further comprising one or more positioning loops disposed on the first surface.

7. The apparatus of claim 6, wherein the one or more positioning loops comprise an elastomeric material.

8. The apparatus of claim 6, wherein the one or more positioning loops comprise a buckle for tightening the one or more positioning loops against a portion of the strap.

9. The apparatus of claim 5, wherein the first surface is substantially planar.

10. The apparatus of claim 5, wherein the second surface is curved.

11. The apparatus of claim 5, further comprising a biocompatible adhesive disposed on the second surface.

12. An apparatus for providing a compressive force to a sclera of a patient, the apparatus comprising:

a strap sized to fit around the outer surface of the sclera, the strap having a first end and a second end disposed opposite the first end;

means for adjustably fixing the position of the first end of the strap relative to the second end of the strap to form a continuous loop surrounding the sclera;

a positioning device having a first surface and a second surface disposed opposite the first surface, the first surface having a positioning loop disposed thereon, the loop configured and arranged to receive the strap and the second surface having a biocompatible adhesive disposed thereon;

wherein the means for adjustably fixing the position of the first end of the strap relative to the second end of the strap comprises a plurality of openings disposed on the strap near the first end; a frame attached to the second end of the strap; a prong pivotally attached to the frame; a loop disposed on the strap near the second end of the strap; and, wherein the first end passes through the frame and the loop and the prong engages with one of the openings to fix the position of the first end relative to the second end.

13. The apparatus of claim 12, wherein the positioning loop comprises an elastomeric material.

14. The apparatus of claim 12, wherein the positioning loop further comprises a buckle for tightening the positioning loop against the strap.

15. The apparatus of claim 12, wherein the second surface is curved.

\* \* \* \* \*